United States Patent
Banerjee et al.

[11] Patent Number: 6,075,592
[45] Date of Patent: Jun. 13, 2000

[54] FIBER-OPTICS BASED MICRO-PHOTOLUMINESCENCE SYSTEM

[75] Inventors: Sonali Banerjee, Eatontown; Chung-en Zah, Holmdel, both of N.J.

[73] Assignee: Telcordia Technologies, Inc., Morristown, N.J.

[21] Appl. No.: 09/174,729

[22] Filed: Oct. 19, 1998

Related U.S. Application Data
[60] Provisional application No. 60/070,261, Dec. 31, 1997.

[51] Int. Cl.⁷ .................................................. G01J 3/30
[52] U.S. Cl. ....................................... 356/318; 250/458.1
[58] Field of Search ..................................... 356/317, 318, 356/417, 418; 250/458.1, 459.1, 461.1, 462.1, 227.11–227.31; 436/518, 172; 385/12, 13; 422/82.05–82.09

[56] References Cited

U.S. PATENT DOCUMENTS

| | | |
|---|---|---|
| 4,346,995 | 8/1982 | Morris . |
| 5,053,617 | 10/1991 | Kakizaki et al. . |
| 5,359,681 | 10/1994 | Jorgenson et al. . |
| 5,631,734 | 5/1997 | Stern et al. . |
| 5,736,410 | 4/1998 | Zarling et al. . |

OTHER PUBLICATIONS

High–Speed Photoluminiscence Mapping of III–V Epitaxial Layers for Light–Emitting Diodes, by W.R. Imler, IEEE Journal of Selected Topics in Quantum Electronics, vol. 1No. 4, Dec. 1995. , Wafer Level Testing for Semiconductor Laser Manufacture via Spatially Resolved Photoluminescence, by G. E. Carver et al., IEEE Journal of Selected Topics in Quantum Electronics, vol. 1, No. 4, Dec. 1995.

*Primary Examiner*—K. P. Hantis
*Attorney, Agent, or Firm*—Joseph Giordano

[57] ABSTRACT

Spatially resolved photoluminescence (PL) apparatus is used for the non-destructive characterization of a semiconductor sample. PL excitation from a diode laser is transmitted through a dichroic coupler and, in turn, over a fiber to a fiber collimator wherein the laser light is collimated into a pump beam prior to entering an air path. The air path is composed primarily of an objective lens. The objective lens focuses the pump beam on the sample surface. The photoluminescence signal emitted by the sample travels the same path but in the opposite direction as the pump beam and is collected by the same fiber as a reflected signal. The dichroic fiber coupler is used to separate the return signal from the pump beam with a low insertion loss for each beam. The return PL signal is fed to an optical spectrum analyzer using a single mode fiber connected to the coupler. The sample is placed on a rotational stage capable of x, y and z movement under computer control.

4 Claims, 2 Drawing Sheets

FIBER-OPTICS BASED MICRO-PHOTOLUMINESCENCE SYSTEM

CROSS-REFERENCE TO RELATED APPLICATION

This a nonprovisional application of provisional application Serial No. 60/070,261, filed Dec. 31, 1997.

BACKGROUND OF THE DISCLOSURE

1. Field of the Invention

This invention relates to electro-optical measurement systems and, more particularly, to apparatus for characterizing the semiconductor properties of a sample using the photoluminescence of the sample upon excitation by a photon source.

2. Description of the Background Art

A photoluminescence (PL) measurement is a non-contact, non-destructive method for characterizing semiconductor materials and device structures, and is extensively used as both a diagnostic and quality control tool in semiconductor research and development as well as in the semiconductor manufacturing environment. Whenever a semiconductor material is excited with high energy photons (higher than the bandgap of the semiconductor) from a laser probe, photo-excitation of carriers is effected. These carriers recombine through different processes and emit optical photons of specific energy and spectral distribution which are characteristics of the recombination processes in the material system and give vital information about the optical quality and the bandgap wavelength of the material. The PL spectra thus give characteristic information about the mechanism and the efficiency of the radiative recombination processes.

In recent years, new growth techniques such as Molecular Beam Epitaxy (MBE) and Metallorganic Chemical Vapor Deposition (MOCVD) have been introduced to grow epitaxial material for very sophisticated optoelectronic devices, such as wafers. To achieve good performance and better yield on the wafers, it is very important to obtain uniform material quality for the entire wafer. Besides, the selective area growth and the shadow mask technique are new methods to spatially change the material composition and thickness for photonic device integration such as modulator-laser integration and laser-beam expander integration. The quality control and process development of optoelectronic material mentioned above require PL measurements with high spatial resolution.

Many different arrangements have been employed to characterize the wafers as well as finished devices. Most of these arrangements employ techniques which require a dedicated apparatus with very sophisticated optical and electronic instrumentation. In a representative version of mapping the PL, a single wavelength detection scheme is used where the PL intensity at a fixed wavelength is measured to ensure quality control of the materials. The mapping over the entire wafer area can either be done by keeping the optics fixed and computer controlling the movement of the sample stage (see, for example, the paper entitled "High-Speed Photoluminescence Mapping of III–V Epitaxial Layers of Light-Emitting Diodes", by W. R. Imler, IEEE Journal of Selected Topics in Quantum Electronics, Vol. 1, No. 4, December 1995), or by a combination of beam raster and sample stage movement (see, for example, the paper entitled "Wafer Level Testing for Semiconductor Laser Manufacture via Spatially Resolved Photoluminescence", by G. E. Carver et al., IEEE Journal of Selected Topics in Quantum Electronics, Vol. 1, No. 4, December 1995). The composite picture over the entire area of interest, e.g., over the entire wafer area or over a device, is obtained by advanced signal/video processing techniques for high throughput in a manufacturing environment. In both these techniques, high spatial resolution can be obtained by suitable focusing optics and by spatially filtering the excitation beam with high precision spatial filters (pin-holes). The spatial resolution is determined by the image of the spatial filter on the sample plane. However, if the emission wavelength shifts from the detection wavelength, mapping of the PL intensity at a fixed wavelength is not representative of the optical quality of the material. The reason for this is that there may be spectral variations across the sample which in a fixed wavelength detection system may appear as PL intensity variations. It is therefore necessary in an improved measurement system to obtain complete spectral information.

In systems which are capable of complete spectral information, the major detection system is composed of a high resolution monochromator, detector arrays, multichannel analyzers, and video imagers, all of which are rather expensive and are often dedicated to a single measurement. Moreover, the excitation source is often a bulky gas laser.

Thus, the art is devoid of a PL apparatus and concomitant methodology wherein the excitation and collection optics are common and remain fixed while the sample is placed on a position-controlled stage and, moreover, wherein the measurement components are of the modular, plug-in type so that the components need not be dedicated to the PL measurement, but can be shared with other apparatus to thereby provide cost benefits.

SUMMARY OF THE INVENTION

These shortcomings and other limitations and deficiencies are obviated in accordance with the present invention by deploying a cost-effective, modular arrangement based on single-mode fiber optic components and a semiconductor pump laser.

In accordance with a broad aspect of the present invention, a confocal, micro-photoluminescence apparatus achieves a spatial resolution of ~5 $\mu$m. The source of PL excitation is a high-power diode laser. After passing through a dichroic coupler, the laser light is transmitted over a fiber to a fiber collimator wherein the laser light is collimated into a beam of ~0.5 mm diameter prior to entering an air path. The air path is composed primarily of an objective lens. The objective lens focuses the pump beam to ~10 $\mu$m diameter on the sample surface. The photoluminescence signal emitted by the sample travels the same path but in the opposite direction as the pump beam and is collected by the same fiber as a reflected signal. The dichroic fiber coupler is used to separate the return signal from the pump beam with a low insertion loss for each beam. The return PL signal is fed to an optical spectrum analyzer using a single mode fiber connected to the coupler. The sample is placed on a rotational stage capable of x, y and z movement under computer control. The rotational stage also aids to initially orient the sample.

There are numerous features of the present invention, including the fact that the arrangement takes advantage of off-the-shelf optical fiber optical components and instrumentation developed for optical fiber communication. Since the fiber optic industry is a rapidly advancing area, the apparatus has the benefit of this advancement. Major parts of the apparatus are designed to be in modular form and linked by optical fibers. This approach allows its instruments or components to be shared with other measurement setups to reduce the capital cost without worrying about the optical alignment in free space. Only the free space (air path) of the system needs to be dedicated, which can be built compact and at a very low cost. Therefore it is very attractive for small manufacturers, research and development entities, and university laboratories. If the optical spectrum analyzer is available, the rest of the apparatus can be built at an approximate cost of one tenth or less of present commercially available systems. The unique features and advantages, engendered by the confocal arrangement of the apparatus, are summarized as follow: (1) a fiber optics based modular design to allow the sub-modules such as optical spectrum analyzer to be shared with other measurement setups to minimize the system fixed cost; (2) a pigtailed diode laser is used as a compact pump source; (3) the pump light can be transmitted over a fiber from a remote site and its power can be easily changed by adjusting the laser diode injection current; (4) the pump beam and the return signal share the same focusing optics; (5) the compact design allows easy assembly and alignment; (6) once the optics are aligned for best PL detection, no further adjustment is required over a long period of time; (7) a compact dichroic fiber coupler is used to separate the return signal from the pump beam with a low insertion loss; (8) since it is a modular design, it can be easily adapted to be used in any other wavelength region by simply changing the pump laser, fibers, the dichroic fiber filter, and the objective lens appropriately with very little additional cost; (9) the fiber input/output feature can also be utilized for remote applications; and (10) the apparatus is controlled by a personal computer to do sample stage movement, spectral measurements and data acquisition.

BRIEF DESCRIPTION OF THE DRAWINGS

The teachings of the present invention can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
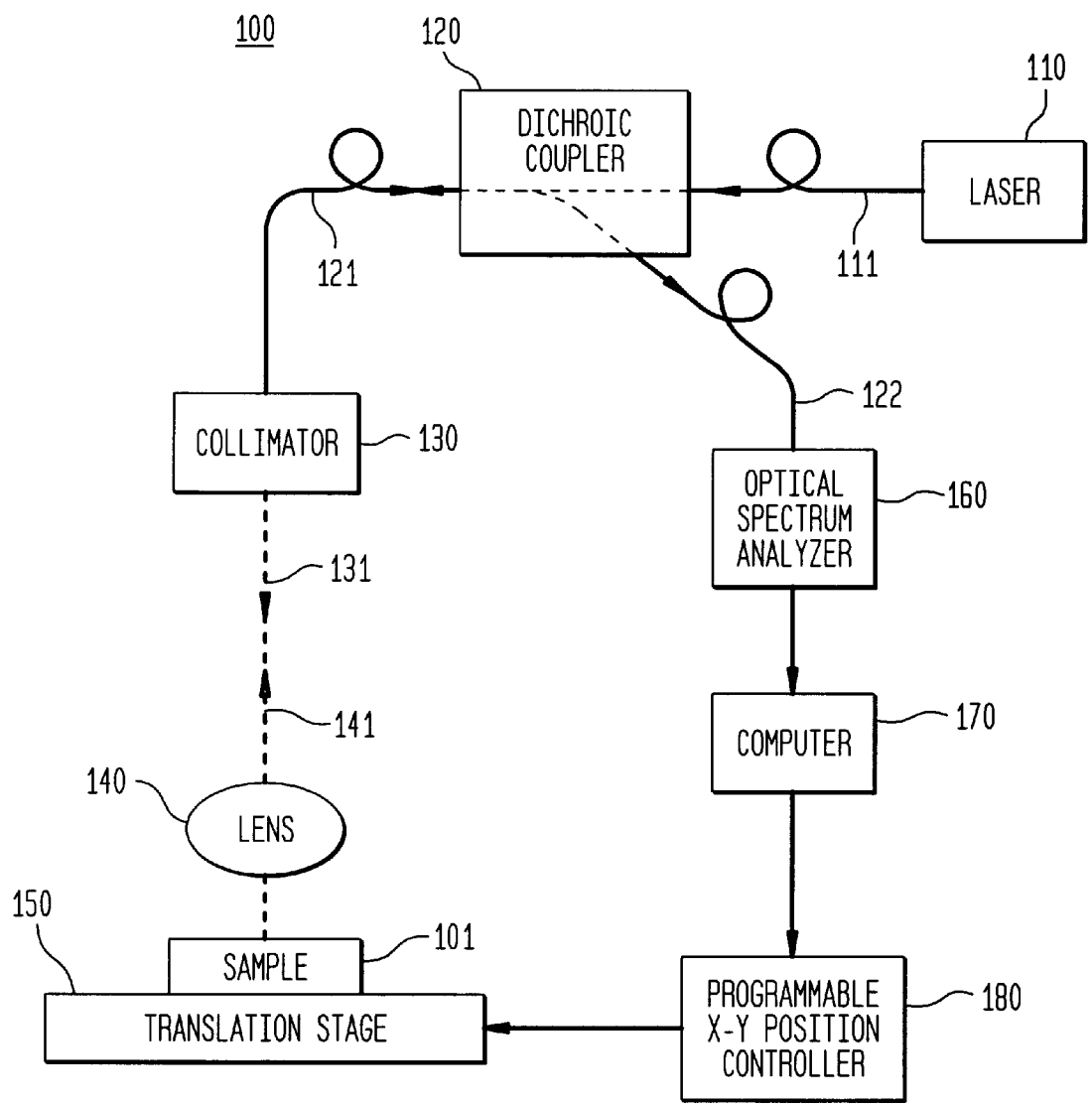
FIG. 1 is an illustrative embodiment of the confocal PL measurement apparatus in accordance with the present invention.

Illustrative spatially resolved Photoluminescence (SRPL) measurement apparatus 100 is shown in FIG. 1, which depicts an electro-optical, fiber-based measurement system capable of measuring PL spectra of sample 101 with ~5 $\mu$m spatial resolution. Source 110 of PL excitation, which generates a "pump beam", is in a preferred embodiment a compact, temperature controlled 980 nm pigtailed diode laser (e.g., model QLM9S-470-209 of the Lasertron Corp.). The pump beam is transmitted over single mode fiber 111 with ~10 $\mu$m core diameter to dichroic coupler 120. A typical power density of the pump beam emitted by source 110 is ~5×10$^4$ W/cm$^2$, which is small enough to prevent irreversible thermal damage to sample 101. The pump beam power can be changed by controlling the laser diode injection current.

The pump beam transmitted by fiber 111 is passed through dichroic fiber coupler 120 (e.g., model WD913 by JDS Corp.) to fiber 121 connected to coupler 120 and, in turn, the output of fiber 121 is collimated to a diameter of ≦0.5 mm using, illustratively, Graded Index (GRIN) lens fiber collimator 130 (e.g., model CFS-N-1550 by Optics for Research). Collimator 130 is mounted so that it can be tilted as well as translated in the x-y plane for easy alignment. The pump beam emitted by collimator 130, shown by reference numeral 131, is transmitted through free space (indicated by a dashed line) and focused on single objective lens 140 (e.g., model F-L40B by the Newport Corp.). Sample 101 is arranged within the focal range of lens 140.

With single lens focusing as implemented by apparatus 100, the spatial resolution of the pump beam is limited by the focusing optics according to the relationship $w_0 \approx \lambda f/(w\pi)$, where $w_0$ is the 1/e$^2$ radius of the focused laser spot, $\lambda$ is the wavelength of the pump beam, f is the focal length of the objective lens, and w is the 1/e$^2$ radius of the laser spot at the surface of lens 140. For apparatus 100, objective lens 140 focuses the pump beam to a 5 $\mu$m±0.5 $\mu$m diameter spot on the top surface of sample 101 placed directly below lens 140 at a distance of ~4.5 mm. Objective lens 140 is anti-reflection coated at 1550 nm for the best collection of the PL signal emitted by sample 101. The PL signal emitted by sample 101 is in the 1100–1630 nm range; this PL signal propagates along the same path as the pump beam, but in the reverse direction shown by beam 141. Beam 141 is collected by fiber 121 and is delivered as a return or reflected signal to dichroic fiber coupler 120. Dichroic coupler 120 is used to isolate the reflected beam from the transmitted beam with a low insertion loss (e.g., about 0.4 dB for both the pump beam and the reflected beam). The return signal is delivered to optical spectrum analyzer 160 via fiber 122 connected to coupler 120.

Sample 101 is placed on mechanized sample translation stage 150, which is capable of x, y, and z (vertical direction) movement with approximately a 1 $\mu$m resolution which can be controlled in the x and y directions using programmable motion controller 180. The movement of stage 150 is controlled by computer 170, and spectral measurement data as obtained from analyzer 160 may be analyzed by computer 170.

Alignment of Sample

Figure 2:
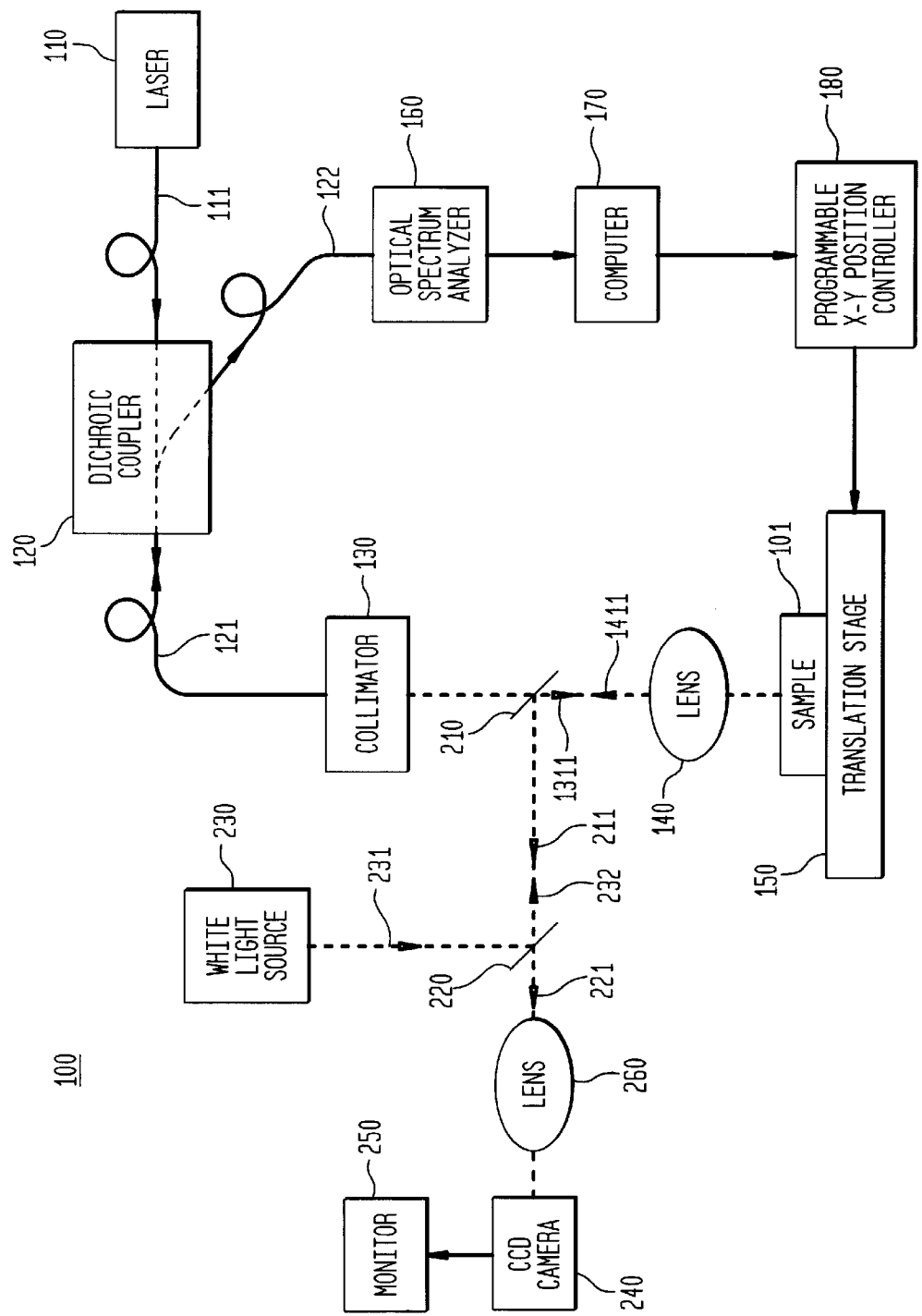
FIG. 2 depicts, in overlay fashion, components augmenting the components of FIG. 1 to effect alignment.

With reference to FIG. 2, components that augment apparatus 100 of FIG. 1 to effect initial alignment of sample 101 are beam splitter 210, beam splitter 220, white light source 230, camera 240, and monitor 250, which components cooperatively interact with mechanized stage 150 for the initial alignment of sample 101 parallel to the x or y axis, as follows. Light source 230, with source 110 turned off, is used to illuminate the surface of sample 101 in order to image the sample surface onto high resolution CCD camera 240 for the visual alignment of sample 101. Beam 231 from source 230 is split by beam splitter 220 (e.g., model 10QM20LP.31/50 by Newport) to form beam 232 impinging on beam splitter 210, (e.g., model 483882-085 by VWR), which has ~5–10% reflectivity. In turn, beam 232 is split to form beam 1311, which is reflected as beam 1411. Reflected beam 1411 is split by beam splitter 210 to obtain beam 211 which impinges on beam splitter 220. The transmitted portion of beam 211, appearing as beam 221, is focused by lens 260 (model KBX166 by Newport) and is detected by camera 240, and then the image is viewable on monitor 250. Thus, monitor 250 presents the visible image of sample 101 for controlling the placement of sample 101 on mechanized stage 150.

Alignment of Components

Reflected signal 141 from sample 101 at room temperature is usually quite weak as compared to the impinging pump beam 131. It is therefore important to align the optical path such that maximum reflected photoluminescence can be collected. The alignment of electro-optical arrangement 100 involves the alignment of fiber collimator 130 to be substantially perpendicular to the plane of sample 101 in the illustrative configuration. The paths of pump beam 131 and reflected beam 141 are to be as perfectly matched as possible. This requires that pump beam 131 is propagated normally through the center of objective lens 140 without any tilt. To achieve alignment, tilt correction as well as x and y motions are effected on collimator 130. The surface of sample 101 is brought in the focal plane objective lens 140 by the z-movement of stage 150. Initial alignment is done using, for example, a 632 red He—Ne laser as source 110 and a visual coalescing of the pump beam 131 and reflected beam 141. For finer alignment for the best collection of the PL signal at 1550 nm, a highly reflecting surface temporarily replaces sample 101. Also, a 1550 nm laser is temporarily used as for pump source 110 in place of the 980 nm laser. Moreover, dichroic coupler 120 is temporarily replaced by a 2×2 3 dB coupler to measure the signal reflected by the reflecting surface. The intensity of the reflected beam 141 is maximized by fine tuning the tilt and focusing of collimator 130. Typically a power meter (not shown) is attached to the port on the 2×2 coupler receiving the reflected beam to measure the power in the reflected beam. The outcome of the alignment procedure ensures that the focusing optics are well aligned to detect the weak PL emission/reflected signal between 1100–1650 nm from sample 101.

Although various embodiments which incorporate the teachings of the present invention have been shown and described in detail herein, those skilled in the art can readily devise many other varied embodiments that still incorporate these teachings.

What is claimed is:

1. Apparatus for characterizing the photoluminescence properties of a semiconductor sample, said apparatus comprising a translation stage on which the sample is mounted, an optical spectrum analyzer, a laser source of photoluminescence excitation for generating a light beam, a dichroic coupler having three ports, a first optical fiber connecting said laser source to a first of said ports, a second optical fiber connecting said optical spectrum analyzer to a second of said ports, a collimator for producing a collimated beam, a third optical fiber connecting said collimater to a third of said ports, and an objective lens positioned in an air gap between said collimator and said sample for focusing the collimated beam onto said sample to generate a reflected beam representative of the photoluminescent energy emitted by said sample, said collimated beam having a diameter no greater than 0.5 mm and said reflected beam traversing a return optical path through said lens, said collimator, said third optical fiber, said coupler, and said second optical fiber to said optical spectrum analyzer.

2. The apparatus in accordance with claim 1 wherein said collimator and said lens are aligned so that the collimated beam from said collimator and the reflected beam from said sample traverse substantially the same but oppositely-directed optical paths between said collimator and said lens.

3. The apparatus in accordance with claim 2 wherein said lens is a single objective lens and is anti-reflection coated at 1550 nm.

4. In combination with the apparatus recited in claim 1, an arrangement for aligning an optical path in the air gap to maximize the collection of the reflected light by the collimator, said arrangement comprising a first beam splitter interposed between said collimator and said object lens in said air gap, a white light source for generating a white light beam, a second beam splitter, responsive to said white light source for propagating a white beam through said first beam splitter to said lens so as to produce a reflected alignment beam from said sample, a focusing lens for receiving the reflected alignment beam from said sample through said first and said second beam splitters, a camera responsive to said reflected alignment beam from said focusing lens, and a monitor coupled to said camera for viewing said sample to align said sample.

* * * * *